United States Patent [19]

Jackson

[11] Patent Number: 5,747,305
[45] Date of Patent: May 5, 1998

US005747305A

[54] MONOGLYCERIDE PRODUCTION VIA ENZYMATIC GLYCEROLYSIS OF OILS IN SUPERCRITICAL $CO_2$

[75] Inventor: Michael A. Jackson, Morton, Ill.

[73] Assignee: The United States of America, as represented by the Secretary of Agriculture, Washington, D.C.

[21] Appl. No.: 679,368

[22] Filed: Jul. 10, 1996

[51] Int. Cl.$^6$ .................................................. C12P 7/64
[52] U.S. Cl. ........................ 435/134; 435/136; 435/198; 435/921
[58] Field of Search ..................... 435/134, 136, 435/198, 921

[56] References Cited

FOREIGN PATENT DOCUMENTS 71979  5/1960  India.

OTHER PUBLICATIONS

C17 119:202128 (19) Jenssen et al "Proc. Scand. Symp. Lipids" 16th 1991 pp. 237–242.

17PS ABS. Japan 01–108990 (Apr. 26, 1989) Fujimoto et al.
Jenssen et al, "Proc. Scand Symp Lipids", Enzymatic reactions in supercritical carbon dioxide 16th 1991 pp. 237–242.

Castillo, E., Marty, A., Combes, D., and Condoret, J. S., "Polar Substrates for Enzymatic Reactions in Supercritical $CO_2$," *Biotechnology Letters*, vol. 16, No. 2 (Feb. 1994), pp. 169–174.

Holmberg, K. and Osterberg, E. "Enzymatic Preparation of Monoglycerides in Microemulsions," *JAOCS*, vol. 65, No. 9 (Sep. 1988), pp. 1544–1548.

Sonntag, Norman O. V., "Glycerolysis of Fats and Methyl Esters—Status, Review, and Critique," *JAOCS*, vol. 59, No. 10 (Oct. 1982), pp. 795A–802A.

*Primary Examiner*—Herbert L. Lilling
*Attorney, Agent, or Firm*—M. Howard Silverstein; Joseph A. Lipovsky; John D. Fado

[57] ABSTRACT

Production of monoglycerides is enhanced by means of enzymatic transesterification of triglycerides with aliphatic alcohols in a medium of supercritical $CO_2$. Aliphatic primary and secondary alcohols of 1 to 8 carbon atoms may be used without support in supercritical $CO_2$ at temperatures compatible for enzymatic transesterifion of tryglycerides. Utilization of these lower reaction temperatures has the benefit of diminishing the production of undesired side products and thus increasing the reaction efficiency with regard to production of the desired monoglycerides.

10 Claims, No Drawings

MONOGLYCERIDE PRODUCTION VIA ENZYMATIC GLYCEROLYSIS OF OILS IN SUPERCRITICAL CO$_2$

BACKGROUND OF THE INVENTION

1. Field of the Invention

The production of monoglycerides for both food and industrial use has been in practice since before the second world war. The existing processes for production of these compounds have as limitations high energy consumption, relatively low reaction yields, and difficulties in purification of the end product. The present invention relates to the use of an enzymatically assisted glycolytic reaction in a medium of supercritical CO$_2$ to produce these monoglycerides without the drawbacks of the prior art.

2. Description of the Prior Art

The use of monoglycerides in pharmaceutical formulations and prepared foods continues to increase. In the pharmaceutical field, monoglycerides are used as binders in tablets, and as emollients for transdermal, slow-release drugs. In the food industry, they serve to stabilize emulsions in sauces and baked goods. The manufacture of monoglycerides is presently an energy-intensive process involving the heating to 240° C. of a stirred emulsion of vegetable oil and glycerol in the presence of an inorganic catalyst. At the end of the reaction, the mixture is rapidly cooled to minimize reversion of the product which would otherwise significantly decrease the yield. The yield of monoglycerides is usually around 40%, with the product produced suffering from discoloration due to the presence of thermal degradation products. This mixture of free fatty acids, and mono-, di-, and triglycerides is then distilled to yield a food-grade material that is 90% monoglycerides.

Sonntag ("*Glycerolysis of Fats and Methyl Esters-Status, Review and Critique*", JAOCS, vol.59, No.10, pp.795–802;1982) teaches that glycerolysis of fats has historically been accomplished through the use of batch processes involving the mixing of glycerol and fat in the presence of an alkaline catalyst at temperatures ranging from 220° C. to 260° C. in a nitrogen atmosphere. The temperature limitation and the use of nitrogen are for the purpose of minimizing the creation of undesirable side products. Reversion of the desired monoglycerides back to reactant form is minimized by speedy neutralization of the catalyst, cooling of the reaction mixture and removal of the glycerol at the end of the desired reaction period. Yields of these art-practiced systems are in large part constrained by the restricted solubility of glycerol in the fat, which limits the molar excess of glycerol that can physically be present in the reaction mixture to no more than about 140% under the best of conditions. Attempts to enhance solubility, and hence reaction yields, through the use of a solvent system that is mutually compatible with both fats and glycerol, have not resulted in industrially adaptable protocols due to the toxicity of the compounds involved (1,4-dioxane, cresols, phenol and pyridine).

Kochar et al in Indian Patent Specification No. 71979 (1962) disclose the preparation of monoglycerides from glycerol and fatty oils by use of an aqueous solution of carbon dioxide which functions as a catalyst in a reaction occurring at elevated temperatures (100°–300° C.) and a pressure of 20–1000 lbs for 20 minutes to 2 hours. Disclosed advantages for the process include the absence of objectionable catalyst, higher product purity, lack of need for anhydrous reagents and a faster rate of reaction.

Holmberg et al ("*Enzymatic Preparation of Monoglycerides in Microemulsion*", JAOCS, Vol. 65, no.9; September 1988) disclose the preparation of monoglycerides by means of an enzyme catalyzed hydrolysis of the corresponding triglyceride. Microemulsions were formed by use of a hydrocarbon-based solvent system containing the surfactant sodium bis(2-ethylhexyl) sulfosuccinate (AOT). Reactions yields as high as 80% were achieved utilizing a reaction system containing (in weight %): isooctane 83, palm oil 4, phosphate buffer (0.021 M NaH$_2$PO$_4$) 5, and AOT 8. The enzyme, being solubilized in the small water domain, was afforded some protection from the denaturing effect of the solvent. When glycerol was substituted for water component of the system no monoglyceride formation could be seen.

Castillo et al ("*Polar Substrates for Enzymatic Reactions in Supercritical CO$_2$: How to Overcome the Solubility Limitation*"; Biotechnology Letters; 1994) teach the difficulty or inability to dissolve polar compounds in supercritical CO$_2$ and attempts to overcome this through use of complexation with phenylboronic acid and immmobilization of the polar substrate on a silica gel. This work specifically teaches that glycerol, after its adsorption on silica gel could be used to esterify oleic acid in a supercritical CO$_2$ system (83% conversion after 72 hours of reaction). Castillo et al cited this provisional use as being in direct contrast to the work of Diaz et al (1984) in U.S. Pat. No. 4,478,612 which teaches the solubility of glycerol in supercritical CO$_2$ as being so low (0.66 mM at 13.8 MPa and 32° C.; 0.7 mM at 13.8 MPa and 46° C.) as to condemn its direct use for reactions.

While various methodologies for gylcerolysis of oils exist, there remains a need for the creation of alternate viable and cost-effective systems for this purpose.

SUMMARY OF THE INVENTION

We have now discovered a process for the effective production of monoglycerides by means of enzymatic glycerolysis of oils in supercritical CO$_2$. It has been found that aliphatic primary or secondary alcohols may be used, without the need for their immobilization on a silica gel, in supercritical CO$_2$ at temperatures effective for enzymatic conversion of oils to monoglycerides. These methods are advantageous in their ability to attain economically viable rates of reaction without the requirement of high reaction temperatures and the production of devaluing side products associated with them.

In accordance with this discovery, it is an object of the invention to provide a lower cost method of preparing monoglycerides from oils.

Another object is to provide a means of producing monoglycerides without the energy consumption associated with high reaction temperatures and product purification.

Other objects and advantages of the invention will become readily apparent from the ensuing description.

DETAILED DESCRIPTION OF THE INVENTION

The present invention involves the preparation of monoglycerides by means of enzymatic glycerolysis of oils in supercritical CO$_2$. It has now been found that aliphatic primary and secondary alcohols may be sufficiently solubilized in supercritical CO$_2$, without the use of solid support, at temperatures conducive to the utilzation of enzymatic means for glycerolysis of fats.

Triglycerides useable in the reaction include any produced from natural plant or animal sources. An exemplary though non-limitative list of such materials includes seed oils such as corn oil, olive oil, cottonseed oil and soybean oil, and animal fats and oils including tallow and lard; with those materials containing higher concentrations of triglycerides being preferred from a standpoint of efficiency and economics. Transesterification of the triglyceride is done with one or more aliphatic primary or secondary alcohols. Suitable compounds include those possessing straight or branched chains of one to eight carbons, with those possessing one to four carbon atoms being preferred. An exemplary but non-limitative list of useable alcohols includes methanol, ethanol, propanol, isopropanol, butanol, isobutanol, sec-butanol, pentanol, isopentanol, hexanol, heptanol, octanol, glycerol, 1,2-propanediol, 1,3-propanediol, ethylene glycol, and propylene glycol.

The molar ratio of alcohol to triglyceride is highly dependent upon the particular alcohol used, but should range from about 2:1 to about 600:1; preferably from about 5:1 to about 350:1. Of the useable alcohols glycerol and methanol are seen to respectively represent the lower and upper thresholds of the taught ranges. Glycerol is useable in conjunction with the triglyceride at molar ratios ranging from about 2:1 to about 20:1; with a preferred range of about 5:1 to about 9:1. Methanol is useable in conjunction with the triglyceride at molar ratios ranging from about 100:1 to about 600:1; with a preferred range of about 250:1 to about 400:1. For the other alcohols utilizable by the invention it is readily determinable by those of ordinary skill in the art what their particular useful and preferred ranges would be.

The triglyceride and alcohol reactants are admixed in a medium of supercritical carbon dioxide at temperatures ranging from about 50° C. to about 80° C., preferably from about 65° C. to about 75° C.; and pressures ranging from about 3000 psi to about 5000 psi, preferably from about 3500 psi to about 4500 psi.

While not wishing to be bound by theory, it is the inventor's belief that the carbon dioxide does not take part in the chemical reaction per se, but rather that it does play an assistive role in the reaction by its enhancement of component flow, mixing and solubilization. The amount of supercritical $CO_2$ to be utilized in the reaction system would be readily determinable by one of ordinary skill in the field and would in large part be dependent upon the particular process scenario desired with regard to equipment utilized as well as the rate and degree of conversion desired. Typical useable flow rates of supercritical $CO_2$ in the reaction system range from about 0.125 to about 25 liters/min of $CO_2$(@STP) per μmol/min of the triglyceride feed. Preferred flow rates of the supercritical $CO_2$ range from about 2 to about 5 liters/min of $CO_2$(@STP) per μmol/min of the triglyceride feed.

The reaction is catalyzed by the use of a lipase that is preferably immobilized, such as by covalent bonding, onto a non-reactive base, such as polyacrylamide, so as to minimize its loss into the reaction system. Due to the powerful inhibitory effect the presence of water has upon the glycerolysis reaction, it is incumbent that none of the reaction feedstreams, as well as the enzyme utilized, either not contain significant amounts of water or bind it sufficiently well so that its level of release into the system not appreciably interfere with the rate of the glycerolysis reaction. The maximum level of reactively available water should be less than or equal to about 0.25% by weight of the reactants; with a preferred level being less than or equal to about 0.1% by weight of the reactants. Any lipase not requiring the presence of water may be used; exemplary among such is Novozym 435™ (*Candida antarctica*) marketed by Novo Nordisk (Danbury, Conn.). This product is available with a declared activity of 7000 Propyl Laurate Units(PLU)/g; with this activity being determined on the basis of a batch ester synthesis assay involving a substrate of 1-Propanol, Lauric acid at a temperature of 60° C. and a time of 15 minutes. The ester formation is calculated based on the acid values, as determined by titration, of the reaction mixture measured both before and after the aforementioned incubation. The amount of enzyme to be utilized would be readily determinable by one of ordinary skill in the field and would in large part be dependent upon the particular enzyme as well as the specific process scenario desired. While not wishing to be limited thereto, enzyme loads of Novozym 435™ projected as useable in the process of the instant invention range from about 1400 PLU to about 280,000 PLU per μmol/min of the triglyceride flowstream; with a range of from about 10,000 PLU to about 40,000 PLU per μmol/min of the triglyceride flowstream being preferred.

The reaction is carried out in an inert atmosphere using a vessel made of non-reactive material such as glass or stainless steel. Product separation is accomplished by any art-known means which typically includes initial depressurization, wherein the $CO_2$ is collected as a gas and optionally recycled, followed by a water wash of the remaining liquid product to remove any unreacted alcohol. The resultant product, comprising the glyceride-containing fraction, contains from about 40% to about 90% monoglycerides, preferably from about 75% to about 87% monoglycerides, with the balance being comprised of diglycerides and triglycerides.

While described in terms of a continuous reaction, it is within the ambit of the skilled practitioner to modify the process into either a semi-continuous or batch mode. Further, any assistive technique increasing the efficiency or speed of reaction, such as mechanical mixing, may be applied to the process for its art-expected effects.

The following example is intended to further illustrate the invention and is not intended to limit the scope of the invention which is defined by the claims.

All percentages herein disclosed are by weight unless otherwise specified.

EXAMPLE 1

Triglyceride sources in the form of corn, soybean, cottonseed and olive oils were transesterified with the alcohols: glycerol, ethylene glycol and 1,2-propanediol. These reagents were used without further purification. Novozym 435™ (*Candida antarctica*), described by the manufacturer as having 7000 units/g toward propyl laurate was purchased from Novo Nordisk (Danbury, Conn.), was used as a catalyst in the reaction.

A rapid screen for reactivity of the enzyme and each substrate was performed using an Isco SFX 2–10 extractor. Reactants (50 mg of oil and 50 mg of alcohol) and lipase (1 g Novozym 435™) were placed inside a 10 mL extraction cell, heated and pressurized to reaction conditions, and allowed to react for a period of 15–60 minutes at which time the products were removed into a receiver. Corn, cottonseed, olive, and soybean oils were all found to undergo the glycerolysis reaction in a similar manner. Conditions were optimized for soybean oil. The reaction occurred at temperatures of 40°–70° C. and pressures of 20.7–34.5 MPa. 27.6 MPa and 70° C. were found to be optimal. The water level in the system was minimized by drying the catalyst under flowing carbon dioxide to 0.3 wt % and using glycerol that was 0.7 wt % water. Added water content of 0.3 vol % in carbon dioxide decreased monoglyceride yield by 82%.

For the reactions, Novozym 435™ (10 g) was placed in a stainless steel vessel (0.8×10.2 cm) which had ends plugged with glass wool. Reagents were pumped into the carbon dioxide stream using separate syringe pumps (100DX pumps, Isco, Inc., Lincoln, Nebr.). Substrate volume ratios were chosen to give the highest conversion of soybean oil and were as follows (expressed as µL alcohol/µL soybean oil): glycerol, 0.5; 1,2-propanediol and ethylene glycol, 0.75; methanol, 1.2. Carbon dioxide flow rates were controlled by a micrometering valve and measured with a dry test meter. Products were collected after depressurization into a 100 mL round-bottomed flask.

For the glycerolyses, glycerol flow was maintained at 50% of the flow of the soybean oil, representing a 7-fold molar excess of glycerol. Adjusting the flow of soybean oil from 2.5 µL/min. to 50 µL/min. resulted in a decrease in monoglyceride yield from 87% to 48%. All of the glycerolyses were performed using a single 10 g sample of Novozym 435™ that transesterified about 100 mL of soybean oil without loss of activity.

The product monoglycerides were purified using a solid-phase extraction method. The fatty acid profiles were determined by conversion of the monoglycerides and starting soybean oil to fatty acid methyl esters using Novozyme 435™ and methanol; with the profiles of the two materials being the same, indicating that the formation of the monoglyceride is random.

We claim:

1. A method for producing monoglycerides comprising the steps of:

A) reacting a non-immobilized aliphatic primary or secondary alcohol with a triglyceride under non-aqueous conditions in the presence of a lipase catalyst and supercritical $CO_2$ in amounts and under conditions effective for production of monoglycerides; and B) separating the glyceride-containing reaction product therefrom.

2. The method of claim 1 wherein the triglyceride is selected from fats and oils of plant or animal origin.

3. The method of claim 1 wherein the aliphatic alcohol possesses a straight or branched carbon chain of 1 to 8 atoms.

4. The method of claim 1 wherein the aliphatic alcohol and triglyceride are present in molar ratios ranging from about 2:1 to about 600:1.

5. The method of claim 1 wherein the reaction is carried out at a temperature ranging from about 50° C. to about 80° C.

6. The method of claim 1 wherein the reaction is carried out at a pressure ranging from about 3000 psi to about 5000 psi.

7. The method of claim 1 wherein the $CO_2$ is present in the reaction medium in amounts ranging from about 5 to about 1000 moles per millimole of triglyceride reactant.

8. The method of claim 1 wherein the lipase is Novozym 435™.

9. The method of claim 1 wherein separation step B) includes depressurization for removal of $CO_2$ and a subsequent water wash of the remaining product to remove any unreacted alcohol.

10. The method of claim 1 wherein monoglycerides represent from about 40% to about 90% of the glyceride-containing reaction product of step B).

* * * * *